US010735050B2

(12) United States Patent
Yukimasa

(10) Patent No.: US 10,735,050 B2
(45) Date of Patent: Aug. 4, 2020

(54) COMMUNICATION SYSTEM

(71) Applicant: CANON KABUSHIKI KAISHA, Tokyo (JP)

(72) Inventor: Koji Yukimasa, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 16/596,488

(22) Filed: Oct. 8, 2019

(65) Prior Publication Data

US 2020/0127703 A1    Apr. 23, 2020

(30) Foreign Application Priority Data

Oct. 17, 2018 (JP) ................... 2018-196232

(51) Int. Cl.
*H04B 5/00* (2006.01)
*B41J 29/393* (2006.01)

(52) U.S. Cl.
CPC ........... *H04B 5/0012* (2013.01); *B41J 29/393* (2013.01); *B41J 2029/3937* (2013.01)

(58) Field of Classification Search
USPC ........................................................ 455/41.1
See application file for complete search history.

(56) References Cited

U.S. PATENT DOCUMENTS

| 6,956,450 | B1 | 10/2005 | Lohr | |
|---|---|---|---|---|
| 2012/0274426 | A1* | 11/2012 | Shimasaki | H04B 5/0037 333/24 R |
| 2013/0306363 | A1* | 11/2013 | Yukimasa | H05K 9/00 174/376 |
| 2014/0355935 | A1 | 12/2014 | Kuroda | |
| 2015/0207541 | A1* | 7/2015 | Kuroda | H04B 5/0093 455/41.1 |
| 2015/0214631 | A1* | 7/2015 | Yukimasa | H01Q 15/006 343/909 |
| 2017/0054326 | A1* | 2/2017 | Toba | H02J 50/10 |
| 2018/0049313 | A1* | 2/2018 | Liu | H05K 1/0237 |
| 2018/0198490 | A1* | 7/2018 | Yukimasa | H04B 5/0031 |
| 2018/0198491 | A1* | 7/2018 | Shoji | H04B 5/0012 |
| 2019/0245575 | A1* | 8/2019 | Yukimasa | H01Q 9/04 |
| 2019/0266508 | A1* | 8/2019 | Bunyk | G06F 11/0751 |
| 2019/0303242 | A1* | 10/2019 | Kapit | G06F 11/1076 |
| 2020/0028233 | A1* | 1/2020 | Chen | H01P 3/081 |
| 2020/0091867 | A1* | 3/2020 | Goto | H01L 27/18 |

FOREIGN PATENT DOCUMENTS

| EP | 2884672 A1 | 6/2015 |
|---|---|---|
| EP | 3349365 A1 | 7/2018 |
| JP | 8-224232 A | 9/1996 |

* cited by examiner

*Primary Examiner* — Edward F Urban
*Assistant Examiner* — Max Mathew
(74) *Attorney, Agent, or Firm* — Canon U.S.A., Inc. IP Division

(57) ABSTRACT

A communication system performs wireless communication using electromagnetic field coupling between a transmission coupler and a reception coupler and moves at least one of the transmission coupler and the reception coupler so as to change the position in a predetermined direction of the reception coupler relative to the transmission coupler. In the communication system, the greater the distance between an overlap portion where the transmission coupler and the reception coupler overlap as viewed from a vertical direction to the predetermined direction and an input end of the transmission coupler is, the higher the degree of coupling between the transmission coupler and the reception coupler becomes.

10 Claims, 11 Drawing Sheets

COMMUNICATION SYSTEM

BACKGROUND OF THE INVENTION

Field of the Invention

The present invention relates to a technique for performing wireless communication using electromagnetic field coupling.

Description of the Related Art

In recent years, a near-field communication system for performing wireless communication using electromagnetic field coupling between nearby devices have been developed. Japanese Patent Application Laid-Open No. H8-224232 discusses a computed tomography apparatus in which a coupler provided to a rotary frame and a coupler provided to a fixed frame are coupled together using the electromagnetic field coupling so that the couplers can wirelessly communicate captured image data.

There is a demand for improved communication accuracy in a communication system in which a positional relationship between a transmission-end coupler and a reception-end coupler for performing wireless communication changes as in the technique discussed in Japanese Patent Application Laid-Open No. H8-224232. For example, in a case of a transmission-end coupler having a long transmission line, a signal is attenuated in the vicinity of an end portion of the transmission line that is on the opposite side of a signal input end of the transmission line. Thus, if a reception-end coupler is located in the vicinity of the end portion, intensity of a received signal becomes lower than a threshold value of a comparator, so that the signal is not correctly restored by a reception circuit. To avoid this problem, if an amplitude of a signal input to the input end of transmission line is increased, noise that is generated in association with the input signal is also increased. As a result, intensity of the received noise becomes higher than the threshold value of the comparator in the case where the reception-end coupler is located in the vicinity of the input end, so that the noise is contained in the signal restored by the reception circuit.

SUMMARY OF THE INVENTION

According to an aspect of the present invention, a communication system includes a first coupler configured to transmit a signal from one end portion to another end portion in a predetermined direction, a second coupler that is shorter in length in the predetermined direction than the first coupler, a communication control unit configured to control wireless communication using electromagnetic field coupling between the first coupler and the second coupler, and a movement control unit configured to move at least one of the first coupler and the second coupler so as to change a position in the predetermined direction of the second coupler relative to the first coupler, wherein a degree of coupling between the first coupler and the second coupler is higher in a case in which a distance between a portion of the first coupler overlapping with the second coupler as viewed from a vertical direction to the predetermined direction and the one end portion of the first coupler is a first distance than the degree of coupling in a case in which the distance between a portion of the first coupler overlapping with the second coupler as viewed from the vertical direction and the one end portion of the first coupler is a second distance that is shorter than the first distance.

Further features of the present invention will become apparent from the following description of exemplary embodiments with reference to the attached drawings.

DESCRIPTION OF THE EMBODIMENTS

[Configuration of Wireless Communication System]

Figure 1A:
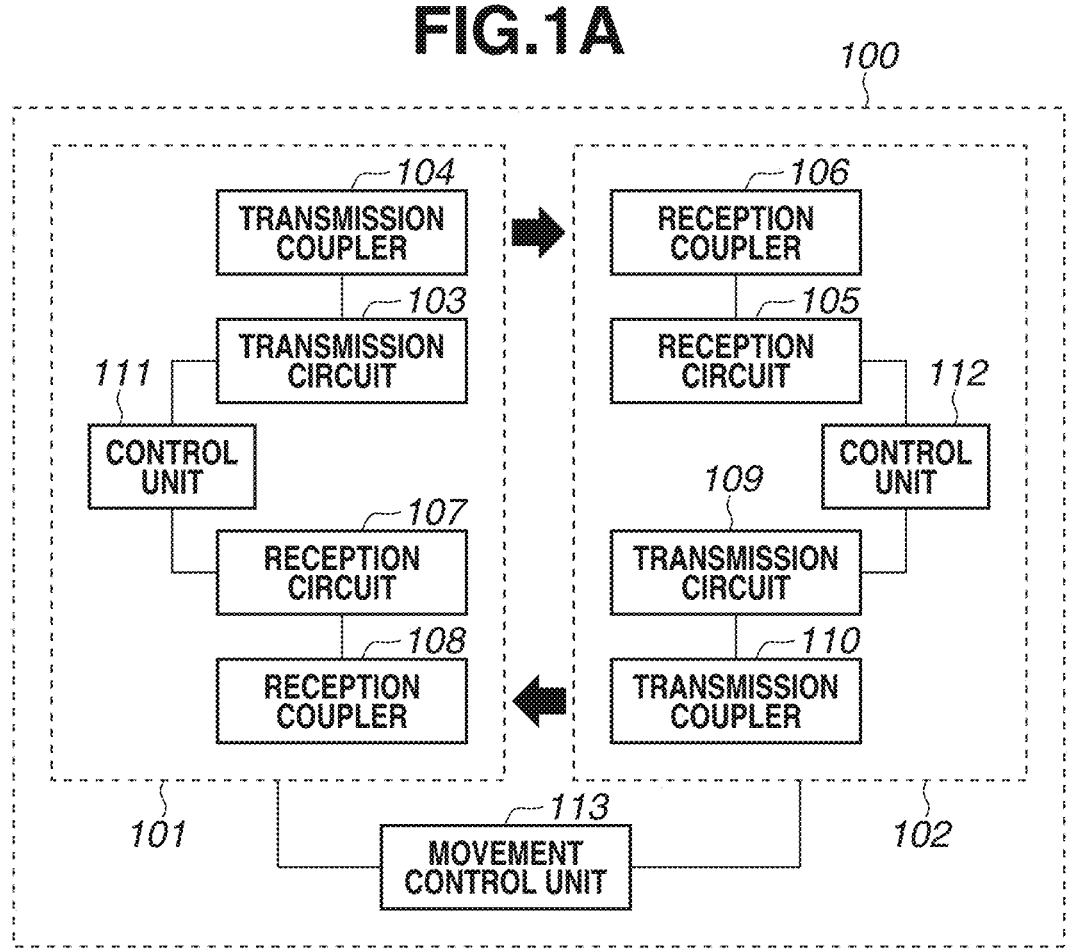
FIGS. 1A and 1B are block diagrams each illustrating an example of a configuration of a wireless communication system.

An exemplary embodiment of the present invention will be described below with reference to the drawings. FIG. 1A illustrates a system configuration of a wireless communication system 100 according to the present exemplary embodiment. The wireless communication system 100 includes communication apparatuses 101 and 102. The communication apparatus 102 wirelessly communicates with the communication apparatus 101. The communication apparatus 101 includes a transmission circuit 103, a transmission coupler 104, a reception circuit 107, a reception coupler 108, and a control unit 111. Similarly, the communication apparatus 102 includes a reception circuit 105, a reception coupler 106, a transmission circuit 109, a transmission coupler 110, and a control unit 112. The communication apparatuses 101 and 102 may also be first and second portions of a single apparatus.

The wireless communication system 100 according to the present exemplary embodiment includes a structure for supporting the communication apparatuses 101 and 102 to maintain a predetermined positional relationship (e.g., positional relationship in which a transmission coupler and a reception coupler face each other) between the communication apparatuses 101 and 102. More specifically, the communication apparatus 101 is a print head portion of a printer and the communication apparatus 102 is a main body portion of the printer. In another example, the communication apparatus 101 is a line head portion in a factory and the communication apparatus 102 is a rail of a line in the factory. However, application of the wireless communication system 100 is not limited to those described above.

The transmission coupler 104 is coupled with the reception coupler 106 using electromagnetic field coupling so that the transmission coupler 104 functions as an antenna for establishing wireless communication between the communication apparatuses 101 and 102. The transmission coupler 110 is coupled with the reception coupler 108 using the electromagnetic field coupling so that the transmission coupler 110 functions as an antenna for establishing wireless communication between the communication apparatuses 101 and 102. The electromagnetic field coupling in the present exemplary embodiment includes both electric field coupling and magnetic field coupling. More specifically, wireless communication between the couplers can be performed using the electric field coupling, the magnetic field coupling, or both.

The control unit 111 of the communication apparatus 101 controls the transmission circuit 103 to transmit data to the communication apparatus 102, and controls the reception circuit 107 to receive data from the communication apparatus 102. Similarly, the control unit 112 of the communication apparatus 102 controls the transmission circuit 109 to transmit data to the communication apparatus 101, and controls the reception circuit 105 to receive data from the communication apparatus 101. More specifically, the control units 111 and 112 perform communication control so that data is communicated between the communication apparatuses 101 and 102. The control unit 111 can control a functional unit (not illustrated) of the communication apparatus 101 based on data received by controlling the reception circuit 107. Similarly, the control unit 112 can control a functional unit (not illustrated) of the communication apparatus 102 based on data received by controlling the reception circuit 105. Examples of the functional units (not illustrated) include a display control unit configured to display an image on a display unit based on received data and a transfer unit configured to transfer the received data to an external apparatus.

The transmission circuit 103 generates an electric signal based on control performed by the control unit 111 and inputs the electric signal to the transmission coupler 104. Similarly, the transmission circuit 109 generates an electric signal based on control performed by the control unit 112 and inputs the electric signal to the transmission coupler 110. The reception circuit 107 restores a voltage generated at the reception coupler 108 using the electromagnetic field coupling in response to input of an electric signal to the transmission coupler 104 into an electric signal via a comparator, and transmits the electric signal to the control unit 111. Similarly, the reception circuit 105 transmits an electric signal based on a voltage generated at the reception coupler 106 to the control unit 112. As described above, the transmission circuit 103 and the reception circuit 105 control communication using the electromagnetic field coupling between the transmission coupler 104 and the reception coupler 106, and the transmission circuit 109 and the reception circuit 107 control communication using the electromagnetic field coupling between the transmission coupler 110 and the reception coupler 108.

In the present exemplary embodiment, a case of performing wireless communication using a baseband method via a transmission-end coupler and a reception-end coupler will be described. In the baseband method, since modulation and demodulation of an electric signal is unnecessary, a circuit size can be reduced and low-delay communication is performed, but a change in amplitude of a received signal affects communication accuracy. However, the communication method is not limited to the above-described method.

For example, carrier communication can be performed by modulating a carrier wave, which is transmitted from the transmission coupler 104 to the reception coupler 106, with an electric signal generated by the transmission circuit 103. While single-ended signal communication is performed in the present exemplary embodiment, the communication is not limited to the single-ended signal communication, and differential signal communication can also be performed.

A movement control unit 113 moves at least one of the communication apparatuses 101 and 102 in a predetermined direction to change the positional relationship between the transmission-end and reception-end couplers. For example, the movement control unit 113 includes a rail, a motor, and a power source. The rail supports the communication apparatus 101. The motor is used to move the communication apparatus 101 along the rail. The power source supplies power to the motor. However, the configuration of the movement control unit 113 is not limited to the above-described configuration. The movement control unit 113 can directly move the transmission coupler 104, the reception coupler 106, or both, instead of moving the entire communication apparatuses 101 and 102.

Figure 1B:
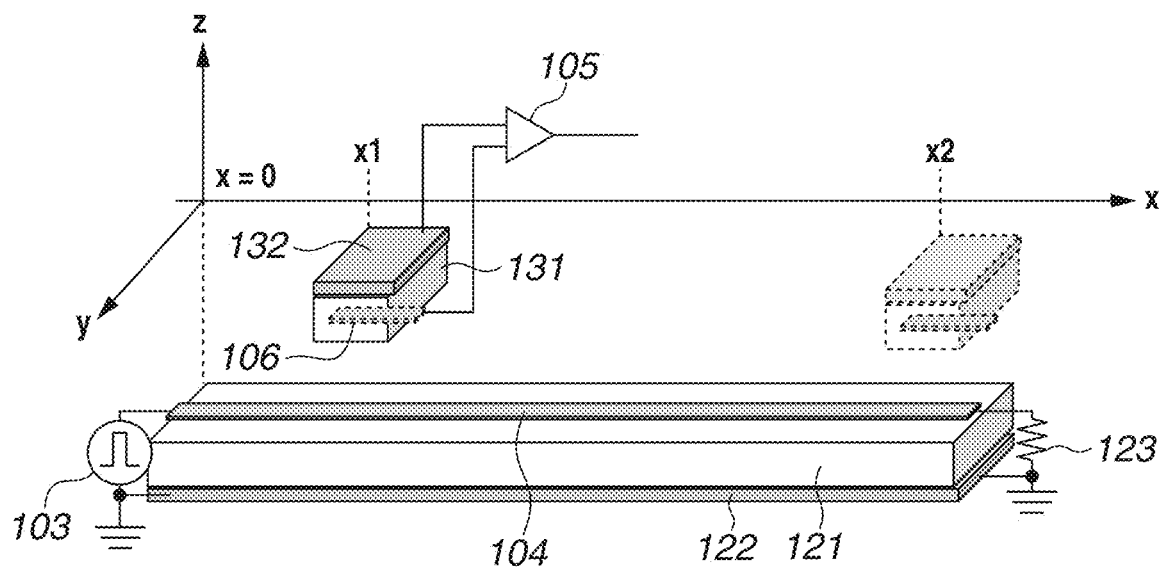

While the communication apparatuses 101 and 102 in FIG. 1A each include two couplers, one for transmission and another for reception, at least one of the communication apparatuses 101 and 102 can include three or more couplers. Further, the configurations of the communication apparatuses 101 and 102 are not limited to the configurations that enable bi-directional communication as illustrated in FIGS. 1A and 1B and can also be configurations for simplex communication in which the communication apparatus 101 includes only a coupler for transmission and the communication apparatus 102 includes only a coupler for reception. Mainly, a configuration (e.g., the transmission circuit 103, the transmission coupler 104, the reception circuit 105, and the reception coupler 106) for transmitting a signal from the communication apparatus 101 to the communication apparatus 102 will be described below. However, a configuration for transmitting a signal from the communication apparatus 102 to the communication apparatus 101 is similar to the below-described configuration. The configuration for transmitting a signal from the communication apparatus 101 to the communication apparatus 102 and the configuration for transmitting a signal from the communication apparatus 102 to the communication apparatus 101 do not have to be the same.

Next, a configuration of the transmission coupler 104 and the reception coupler 106 and their positional relationship will be described below with reference to FIG. 1B. The transmission coupler 104 is a conductive member provided to a surface of a dielectric substrate 121, and a ground 122, which is a metal member, is provided to an opposite surface of the dielectric substrate 121. The transmission circuit 103 is connected to one end portion (input end) of the transmission coupler 104, and a termination resistor 123 is connected to another end portion of the transmission coupler 104. If a signal is input from the transmission circuit 103 to the input end of the transmission coupler 104, the signal is transmitted in a direction (x-direction in FIG. 1B) toward the other end portion of the transmission coupler 104. More specifically, the transmission coupler 104 functions as a signal line of a transmission line.

The reception coupler 106 is a conductive member provided to a surface of a dielectric substrate 131, and a ground 132, which is a metal member, is provided to an opposite surface of the dielectric substrate 131. If a signal flows into the transmission coupler 104, a charge is generated by the electromagnetic field coupling at the reception coupler 106, and the signal is output via the reception circuit 105 connected to the reception coupler 106. More specifically, the reception coupler 106 functions as an electrode constituting a capacitor. However, the configuration of the reception coupler 106 is not limited to the above-described configuration. Alternatively, the reception circuit 107 and a termination resistor can be respectively connected to end portions of the reception coupler 106, and the reception coupler 106 can function as a signal line of a transmission line.

The reception coupler 106 is shorter in length in an extension direction (x-direction in FIG. 1B) of the transmission coupler 104 than the transmission coupler 104. The transmission coupler 104 and the reception coupler 106 have a positional relationship in which the transmission coupler 104 and the reception coupler 106 overlap at least partially when viewed from a direction (z-direction in FIG. 1B) vertical to the signal transmission direction of the transmission coupler 104. The movement control unit 113 changes the relative position of the reception coupler 106 with respect to the transmission coupler 104 in the signal transmission direction (x-direction in FIG. 1B) of the transmission coupler 104. For example, the movement control unit 113 moves the reception coupler 106 within a range (from x=0 to x2) in which the reception coupler 106 faces the transmission coupler 104. However, the movement range is not limited to the above-described range, and the reception coupler 106 can be moved only within a partial range above the transmission coupler 104 or can be moved to the outside of the transmission coupler 104.

Figure 2A:
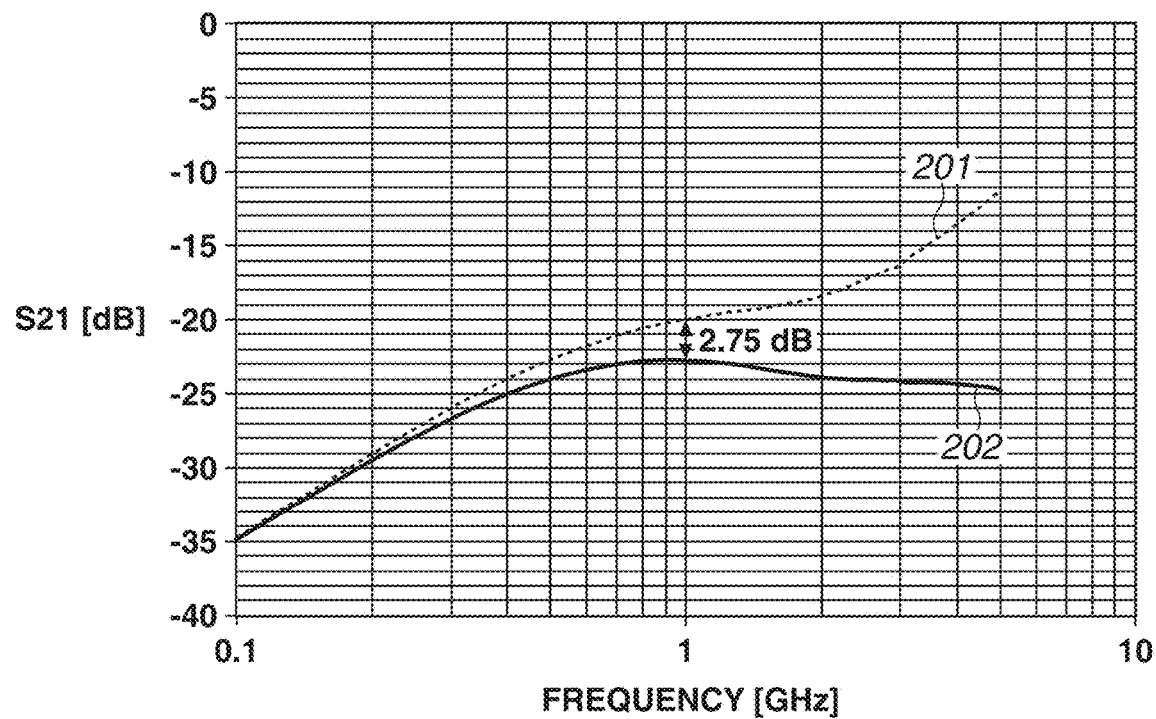
FIGS. 2A and 2B are graphs each illustrating attenuation of a signal transmitted through a transmission line.

FIG. 2A illustrates a simulation result of wireless communication between the transmission coupler 104 and the reception coupler 106 having the configuration illustrated in FIG. 1B. In a graph illustrated in FIG. 2A, the vertical axis represents scattering parameter S21 which indicates a ratio of received power and transmitted power between the transmission coupler 104 and the reception coupler 106, and the horizontal axis represents transmitted/received signal frequency. A dotted line 201 indicates a result of a case in which the reception coupler 106 is positioned at x=0 mm (position of the input end of the transmission coupler 104), whereas a solid line 202 indicates a result of a case in which the reception coupler 106 is positioned at x=1000 mm. At each of the positions x=0 mm and x=1000 mm, the entire reception coupler 106 overlaps the transmission coupler 104 when viewed from the z-direction, and a spacing (distance in the z-direction) between the transmission coupler 104 and the reception coupler 106 is fixed.

In the simulation, a base material of the dielectric substrate 121 and the dielectric substrate 131 is glass epoxy (FR4), a substrate thickness is 1.0 mm, a coupler width is 1.82 mm, and a spacing between the transmission coupler 104 and the reception coupler 106 is 1.0 mm. As illustrated in FIG. 2A, a signal received by the reception coupler 106 is weaker in a case in which the reception coupler 106 is far from the input end of the transmission coupler 104 than in a case in which the reception coupler 106 is close to the input end of the transmission coupler 104, and a difference between the cases increases at higher frequencies. This is due to attenuation of the signal transmitted through the transmission coupler 104. For example, if the frequency is 1 GHz, the intensity of a signal received at the position x=1000 mm is lower than the intensity of a signal received at the position x=0 mm by 2.75 dB.

Figure 2B:
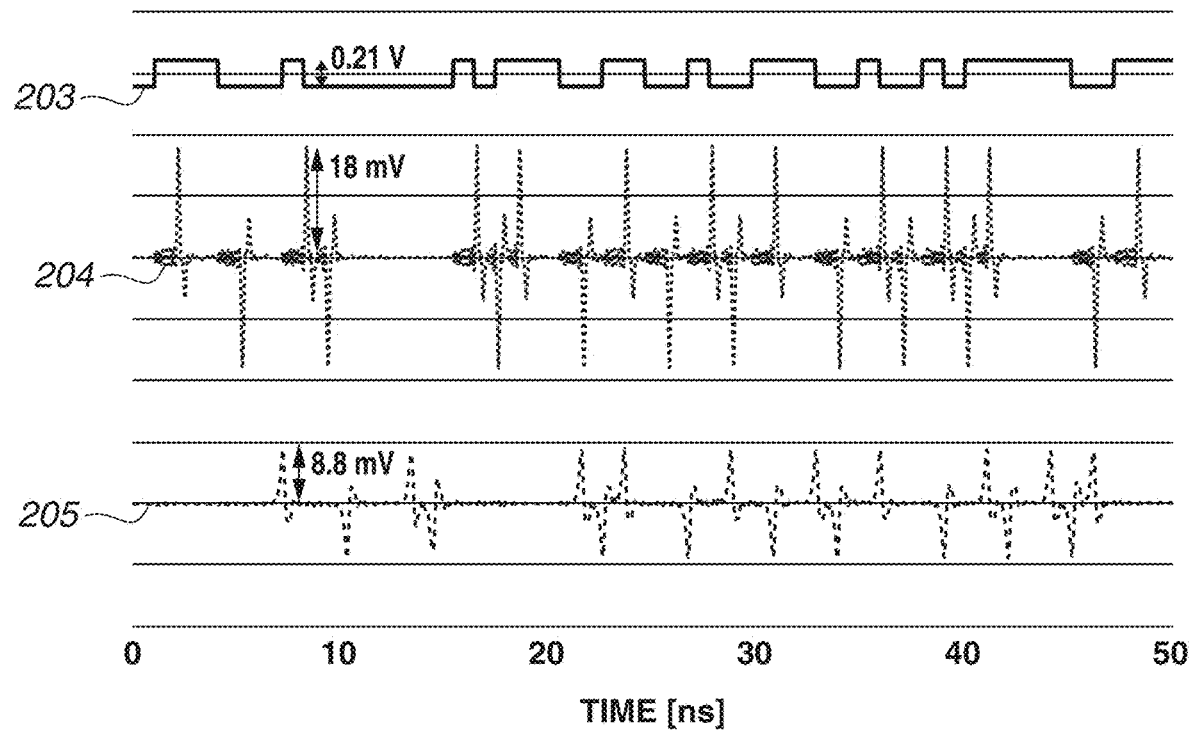

FIG. 2B illustrates a simulation result about a signal communicated between the transmission coupler 104 and the reception coupler 106 having a similar configuration to that in the simulation illustrated in FIG. 2A. In a graph illustrated in FIG. 2B, the vertical axis represents signal voltage, and the horizontal axis represents elapsed time. A waveform 203 indicates a waveform of a signal input to the transmission coupler 104. A waveform 204 indicates a waveform of a signal output from the reception coupler 106 positioned at x=0 mm, and a waveform 205 indicates a waveform of a signal output from the reception coupler 106 positioned at x=1000 mm. In the simulation, a speed of a digital signal input to the transmission coupler 104 is 1.0 Gbps, a signal amplitude is 0.21 V, and the termination resistor 123 is 50 ohms. As illustrated in FIG. 2B, a voltage generated at the reception coupler 106 positioned at x=1000 mm is 8.8 mV, and this is lower than 18 mV, which is a voltage generated at the reception coupler 106 positioned at x=0 mm. The difference in signal timing between the waveforms 204 and 205 is due to a delay in signal transmission at the transmission coupler 104.

[Coupler Facing Area Adjustment]

Figure 3A:
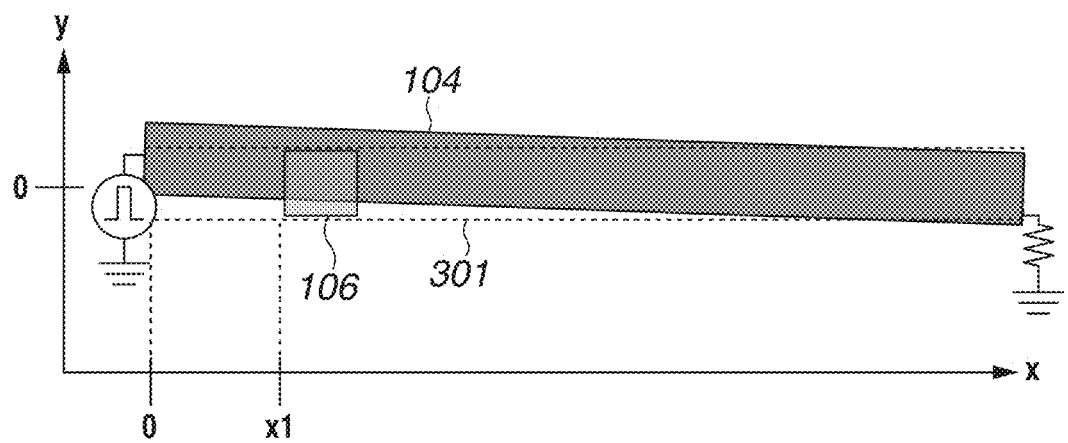
FIGS. 3A and 3B are diagrams illustrating an example of a coupler configuration.
Figure 3B:
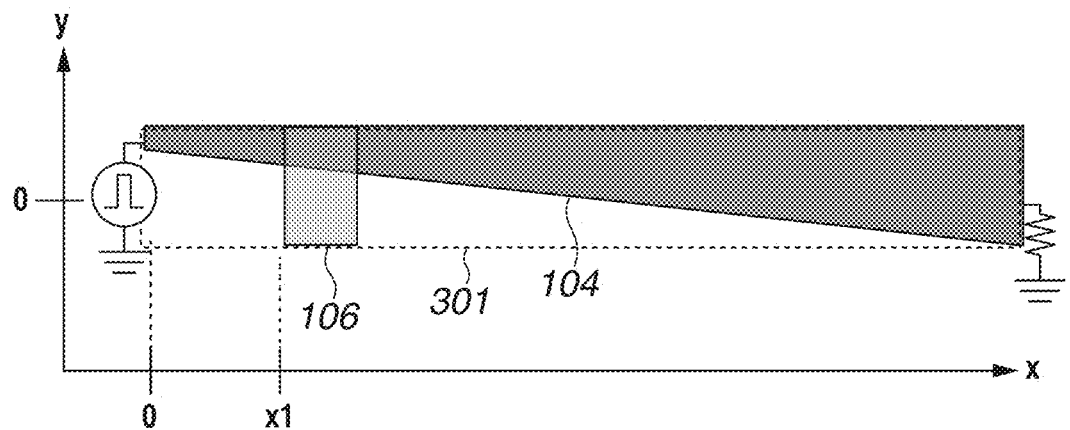

An example of a configuration for preventing a change in received signal intensity that is caused by a change in the above-described positional relationship between the transmission coupler 104 and the reception coupler 106 will be described below. FIG. 3A illustrates a configuration example of a case in which a direction of the transmission coupler 104 is changed from that in FIG. 1B. FIG. 3B illustrates a configuration example of a case in which a shape of the transmission coupler 104 is changed from that in FIG. 1B. FIGS. 3A and 3B illustrate the transmission coupler 104 and the reception coupler 106 viewed from the z-direction, while the dielectric substrate 121 and the ground 122 are omitted. The reception coupler 106 is moved within a movement range 301 surrounded by a dotted line.

In the configuration illustrated in FIG. 3A, a movement direction of the reception coupler 106 and the extension direction of the transmission coupler 104 are not parallel when viewed from the z-direction. Thus, as the position of the reception coupler 106 in the x-direction is closer to the input end of the transmission coupler 104, the difference in y-direction between the transmission coupler 104 and the reception coupler 106 increases. On the other hand, in the configuration illustrated in FIG. 3B, the width of the transmission coupler 104 in the y-direction is not uniform, and the width of the transmission coupler 104 is smaller in the vicinity of the input end than in the vicinity of the other end portion. Thus, in the configurations illustrated in FIGS. 3A and 3B, as the distance (x1 in FIGS. 3A and 3B) between an overlap portion where the transmission coupler 104 and the reception coupler 106 overlap when viewed from the z-direction and the input end of the transmission coupler 104 decreases, an area (facing area) of the overlap portion decreases.

Figure 4:
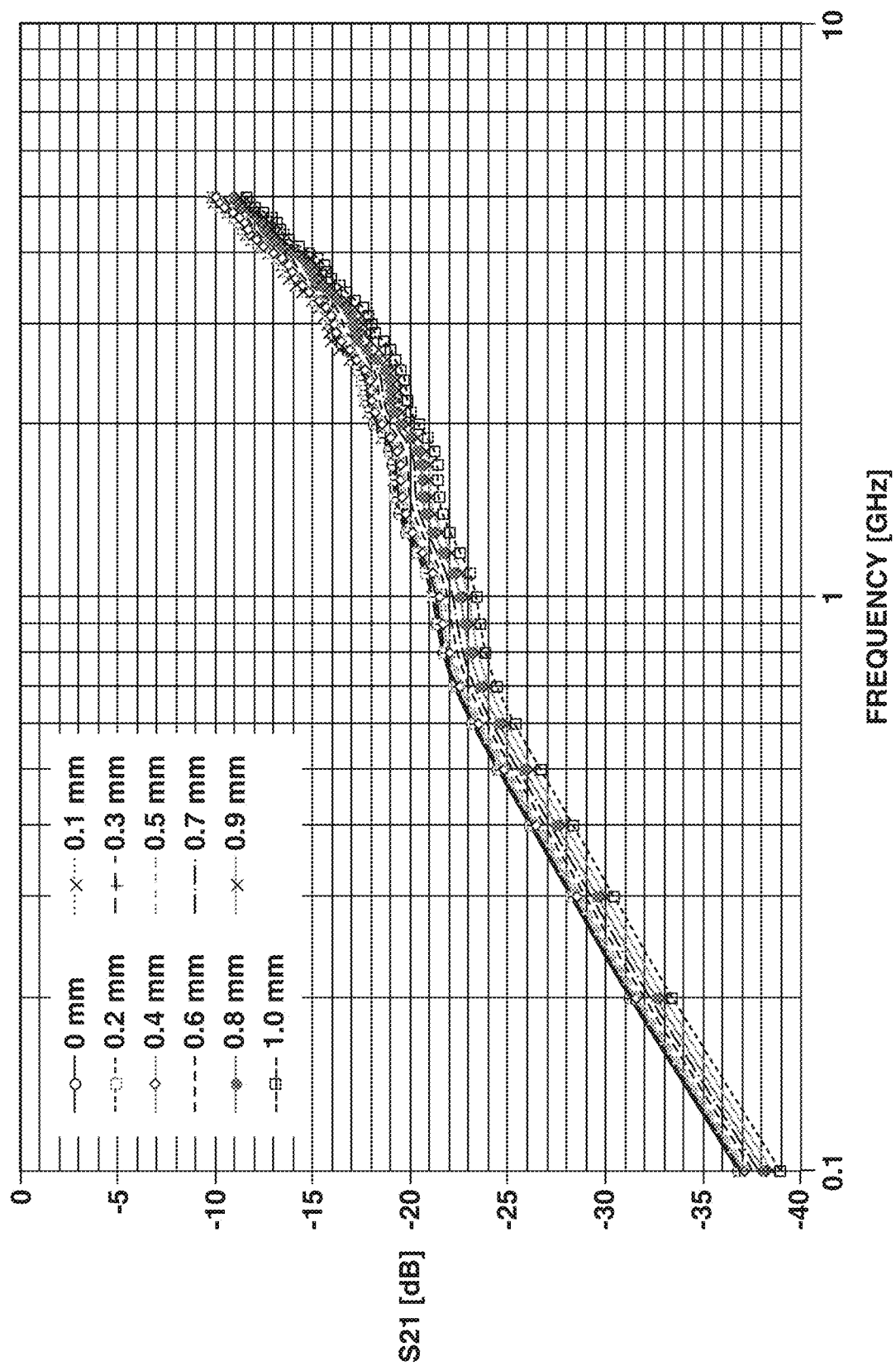
FIG. 4 is a graph illustrating a relationship between a facing area of couplers and a communication signal.

FIG. 4 illustrates a simulation result about wireless communication in a case in which the position of the reception coupler 106 in the x-direction is fixed to x=70 mm while the position of the reception coupler 106 in the y-direction is changed from y=0 mm to y=1.0 mm in the configuration illustrated in FIG. 1B. Since the transmission coupler 104 and the reception coupler 106 have the same width, as the position of the reception coupler 106 in the y-direction becomes farther from y=0 mm, the facing area of the transmission coupler 104 and the reception coupler 106 decreases. The vertical and horizontal axes of the graph in FIG. 4 and the settings about parameters that are not specified herein are similar to those in the simulation illustrated in FIG. 2A. As illustrated in FIG. 4, the smaller the facing area of the transmission coupler 104 and the reception coupler 106 is, the weaker the signal received by the reception coupler 106 becomes. More specifically, the smaller the facing area is, the lower the degree of coupling between the transmission coupler 104 and the reception coupler 106 becomes.

As apparent from the result, in the configurations illustrated in FIGS. 3A and 3B, as the position of the reception coupler 106 in the x-direction becomes farther from the input end of the transmission coupler 104, the degree of coupling between the transmission coupler 104 and the reception coupler 106 increases. Thus, with the configurations illustrated in FIGS. 3A and 3B, a signal received by the reception coupler 106 is prevented from being weakened by attenuation of the signal transmitted through the transmission coupler 104 in the case in which the reception coupler 106 is positioned far from the input end of the transmission coupler 104. In this way, a change in received signal intensity that is caused by a change in the positional relationship between the transmission coupler 104 and the reception coupler 106 is prevented.

Figure 5A:
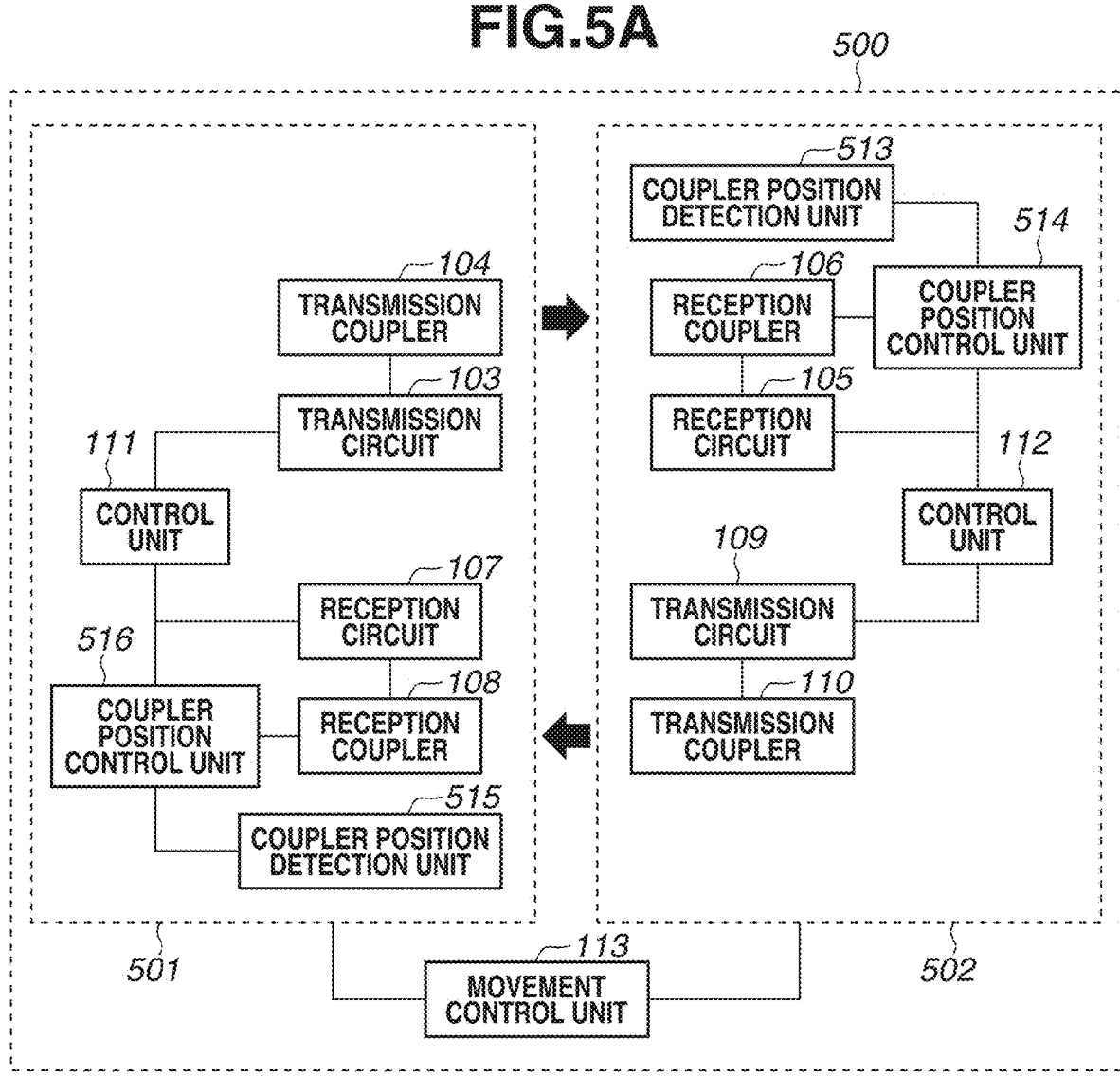
FIGS. 5A and 5B are block diagrams each illustrating an example of a configuration of a wireless communication system.
Figure 5B:
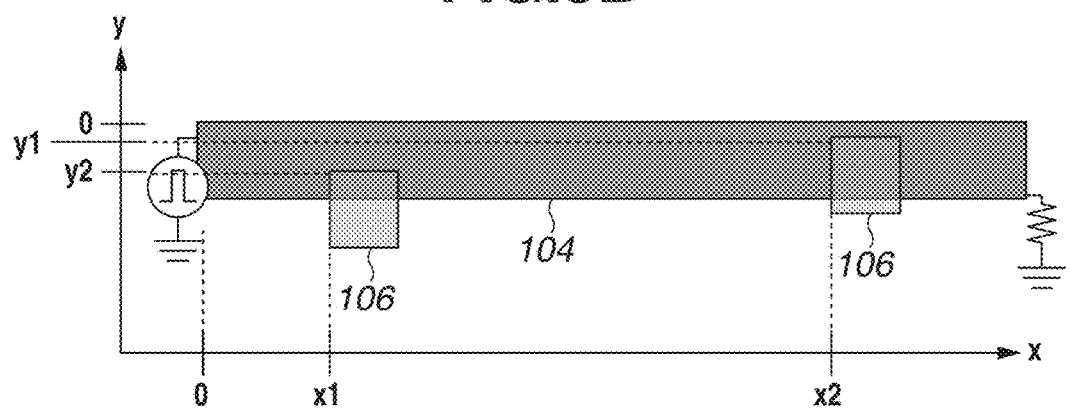

The configuration for adjusting the facing area of the couplers is not limited to the configurations illustrated in FIGS. 3A and 3B. For example, the configurations illustrated in FIGS. 5A and 5B can also prevent a change in the received signal intensity, similarly to the configurations illustrated in FIGS. 3A and 3B. In FIGS. 5A and 5B, each component similar to that in FIGS. 1A, 1B, 3A, and 3B is given the same reference numeral. A wireless communication system 500 illustrated in FIG. 5A includes communication apparatuses 501 and 502. The communication apparatus 501 further includes a coupler position detection unit 515 and a coupler position control unit 516 in addition to the configuration of the communication apparatus 101 illustrated in FIG. 1A. Similarly, the communication apparatus 502 further includes a coupler position detection unit 513 and a coupler position control unit 514 in addition to the configuration of the communication apparatus 102.

The coupler position detection unit 513 detects a relative position of the reception coupler 106 to the transmission coupler 104. The coupler position control unit 514 moves the reception coupler 106 in the y-direction based on the relative position detected by the coupler position detection unit 513 to change the facing area of the transmission coupler 104 and the reception coupler 106. For example, as illustrated in FIG. 5B if the coupler position detection unit 513 detects that the position of the reception coupler 106 in the x-direction is x1, the coupler position control unit 514 moves the reception coupler 106 in the y-direction to y2. On the other hand, if the coupler position detection unit 513 detects that the position of the reception coupler 106 in the x-direction is x2, the coupler position control unit 514 moves the reception coupler 106 in the y-direction to y1.

As described above, the coupler position control unit 514 increases the difference in position in the y-direction between the positions of the transmission coupler 104 and the reception coupler 106 as the distance between the overlap portion where the transmission coupler 104 and the reception coupler 106 overlap when viewed from the z-direction and the input end of the transmission coupler 104 becomes shorter. Consequently, as in the configurations illustrated in FIGS. 3A and 3B, as the position of the reception coupler 106 is closer to the input end of the transmission coupler 104, the facing area of the couplers decreases, and the degree of coupling between the transmission coupler 104 and the reception coupler 106 decreases.

While the movement control unit 113 controls the coupler position in the x-direction and the coupler position control unit 514 controls the coupler position in the y-direction in the example illustrated in FIGS. 5A and 5B, the position control is not limited to the control described above. Alternatively, the movement control unit 113 or the coupler position control unit 514 can control the coupler position in both the x- and y-directions. In the method illustrated in FIGS. 5A and 5B, use of the transmission coupler 104 having a special shape as illustrated in FIG. 3B is unnecessary. In the method illustrated in FIGS. 3A and 3B, the coupler position detection unit 513 and the coupler position control unit 514 are unnecessary, so that the configuration of the communication system can be simplified.

[Adjustment of Spacing Between Couplers]

Figure 6:
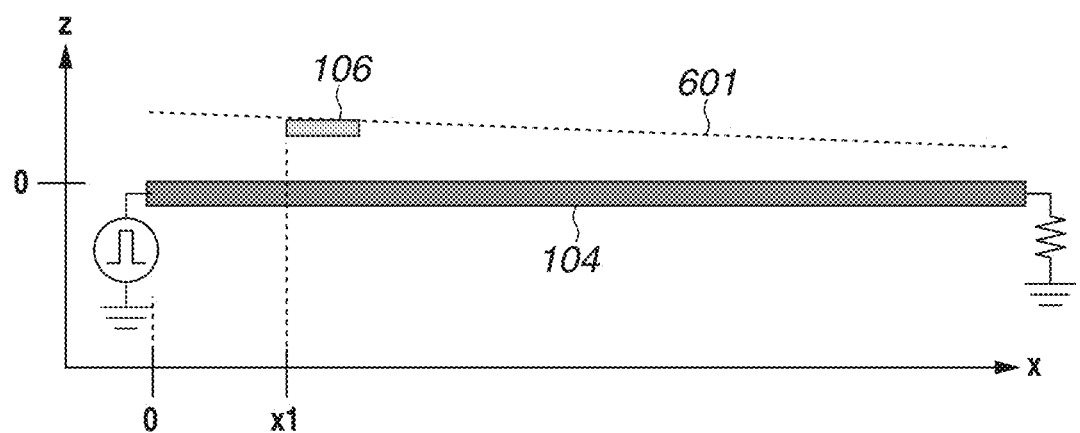
FIG. 6 is a diagram illustrating an example of a coupler configuration.

Another example of a configuration for preventing a change in the received signal intensity that is caused by a change in the positional relationship between the transmission coupler 104 and the reception coupler 106 will be described below. FIG. 6 illustrates an example of a configuration in which the movement direction of the reception coupler 106 is changed from that in FIG. 1B. FIG. 6 illustrates the transmission coupler 104 and the reception coupler 106 viewed from the y-direction, while the dielectric substrate 121 and the ground 122 are omitted. The reception coupler 106 is moved within a movement range 601.

In the configuration illustrated in FIG. 6, the movement direction of the reception coupler 106 and the extension direction of the transmission coupler 104 are not parallel when viewed from the y-direction. Thus, as the position of the reception coupler 106 in the x-direction is closer to the input end of the transmission coupler 104, the spacing between the transmission coupler 104 and the reception coupler 106 in the z-direction increases. Herein, the surface of the dielectric substrate 121 to which the transmission coupler 104 is provided and the movement direction of the reception coupler 106 are not parallel, but the configuration is not limited to the above-described configuration. For example, the dielectric substrate 121 and the reception coupler 106 can be parallel, and a portion of the transmission coupler 104 can be provided to an external layer of the dielectric substrate 121 and another portion of the transmission coupler 104 can be provided to an internal layer of the dielectric substrate 121.

Figure 7:
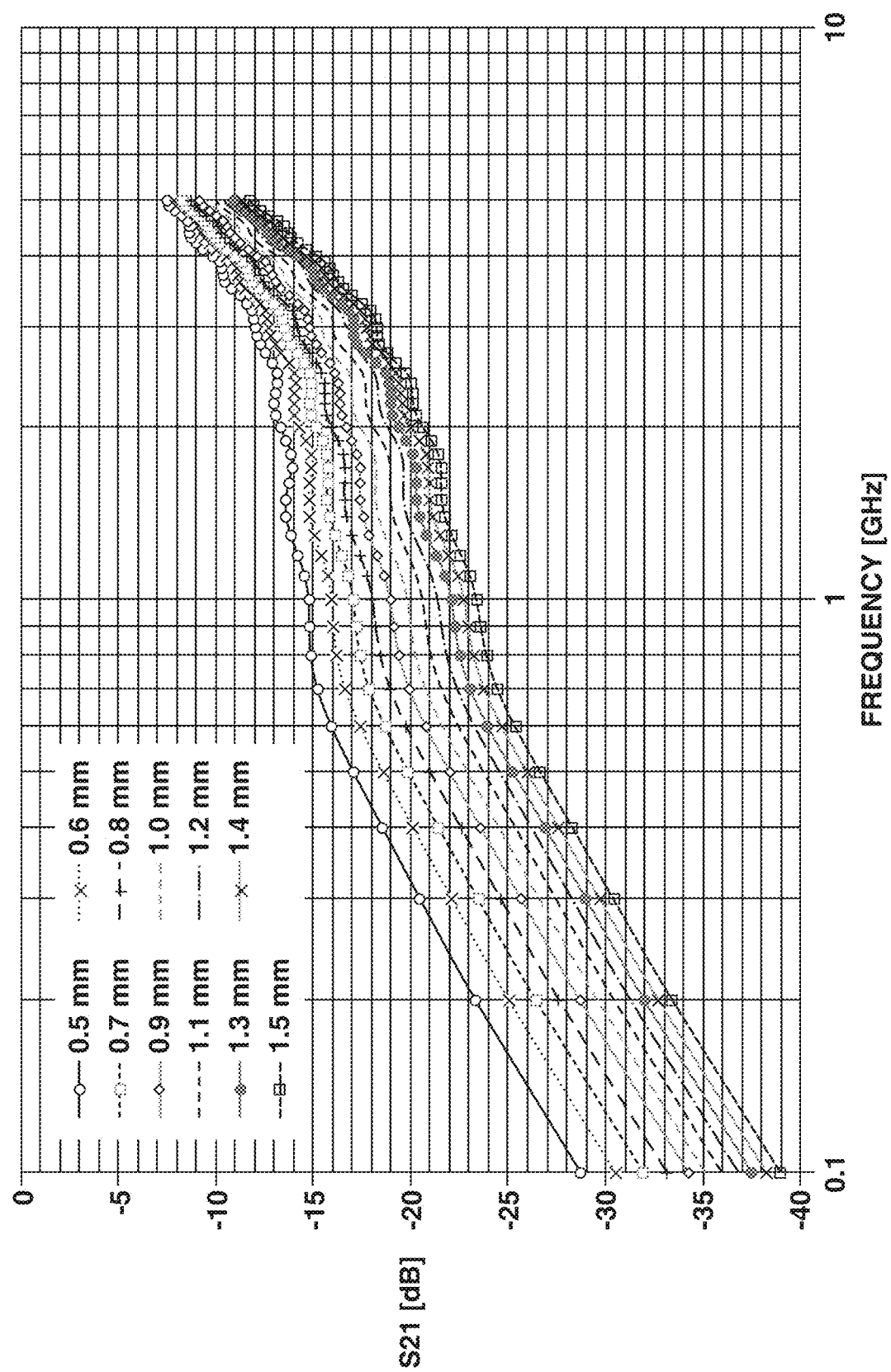
FIG. 7 is a graph illustrating a relationship between a distance between couplers and a communication signal.

FIG. 7 illustrates a simulation result about wireless communication in a case in which the position of the reception coupler 106 in the x-direction is fixed to x=70 mm and the position of the reception coupler 106 in the z-direction is changed from z=0.5 mm to z=1.5 mm in the configuration illustrated in FIG. 1B. The position of the transmission coupler 104 in the z-direction is z=0 mm, and there is no difference in position in the v-direction between the transmission coupler 104 and the reception coupler 106. The vertical and horizontal axes of the graph in FIG. 7 and the settings about parameters that are not specified herein are similar to those in the simulation in FIG. 2A. As illustrated in FIG. 7, the greater the spacing between the transmission coupler 104 and the reception coupler 106 is, the weaker the signal received by the reception coupler 106 becomes. More specifically, as the spacing between the transmission coupler 104 and the reception coupler 106 increases, the degree of coupling between the transmission coupler 104 and the reception coupler 106 decreases.

As apparent from the result, in the configuration illustrated in FIG. 6, the farther the position of the reception coupler 106 in the x-direction is from the input end of the transmission coupler 104, the higher the degree of coupling between the transmission coupler 104 and the reception coupler 106 becomes. Thus, with the configuration illustrated in FIG. 6, a signal received by the reception coupler 106 is prevented from being weakened by attenuation of the signal transmitted through the transmission coupler 104 in the case in which the reception coupler 106 is positioned far from the input end of the transmission coupler 104. More specifically, a change in the received signal intensity that is caused by a change in the positional relationship between the transmission coupler 104 and the reception coupler 106 is prevented.

The configuration for adjusting the spacing between the transmission coupler 104 and the reception coupler 106 is not limited to the configuration illustrated in FIG. 6, and a change in the received signal intensity can also be prevented by the coupler position control unit 514 moving the reception coupler 106 in the z-direction in the wireless communication system 500 illustrated in FIGS. 5A and 5B as in the configuration illustrated in FIG. 6. For example, if the coupler position detection unit 513 detects that the position of the reception coupler 106 in the x-direction is x1 as in FIG. 8, the coupler position control unit 514 moves the position of the reception coupler 106 in the z-direction to z2. On the other hand, if the coupler position detection unit 513 detects that the position of the reception coupler 106 in the x-direction is x2, the coupler position control unit 514 moves the position of the reception coupler 106 in the z-direction to z1.

As described above, the shorter the distance between the overlap portion where the transmission coupler 104 and the reception coupler 106 overlap when viewed from the z-direction and the input end of the transmission coupler 104 is, the greater the spacing between the transmission coupler 104 and the reception coupler 106 in the z-direction is set by the coupler position control unit 514. Consequently, as in the configuration illustrated in FIG. 6, the closer the reception coupler 106 is to the input end of the transmission coupler 104, the lower the degree of coupling between the transmission coupler 104 and the reception coupler 106 becomes. Alternatively, the coupler position control unit 514 can also control the coupler position in the y- and/or x-direction in addition to the coupler position in the z-direction.

Figure 8:
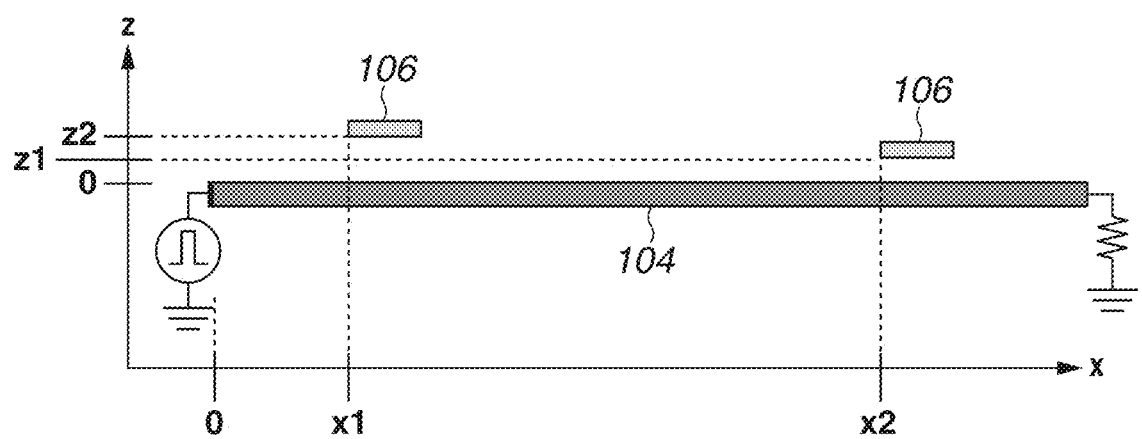
FIG. 8 is a diagram illustrating an example of a coupler configuration.

In the method for adjusting the spacing between the transmission coupler 104 and the reception coupler 106 illustrated in FIGS. 6 and 8, use of the transmission coupler 104 having a special shape as illustrated in FIG. 3B is unnecessary. Further, the y-direction width of a portion in which the transmission coupler 104 and the reception coupler 106 are stored in the communication system 500 is reduced compared to the method illustrated in FIGS. 3A, 5A, and 5B. On the other hand, in the method for adjusting the facing area of the transmission coupler 104 and the reception coupler 106 illustrated in FIGS. 3A, 3B, 5A, and 5B, the z-direction width of the portion in which the transmission coupler 104 and the reception coupler 106 are stored in the communication system 500 is reduced compared to the method illustrated in FIGS. 6 and 8.

[Adjustment by Dielectric Constant of Substrate]

Figure 9:
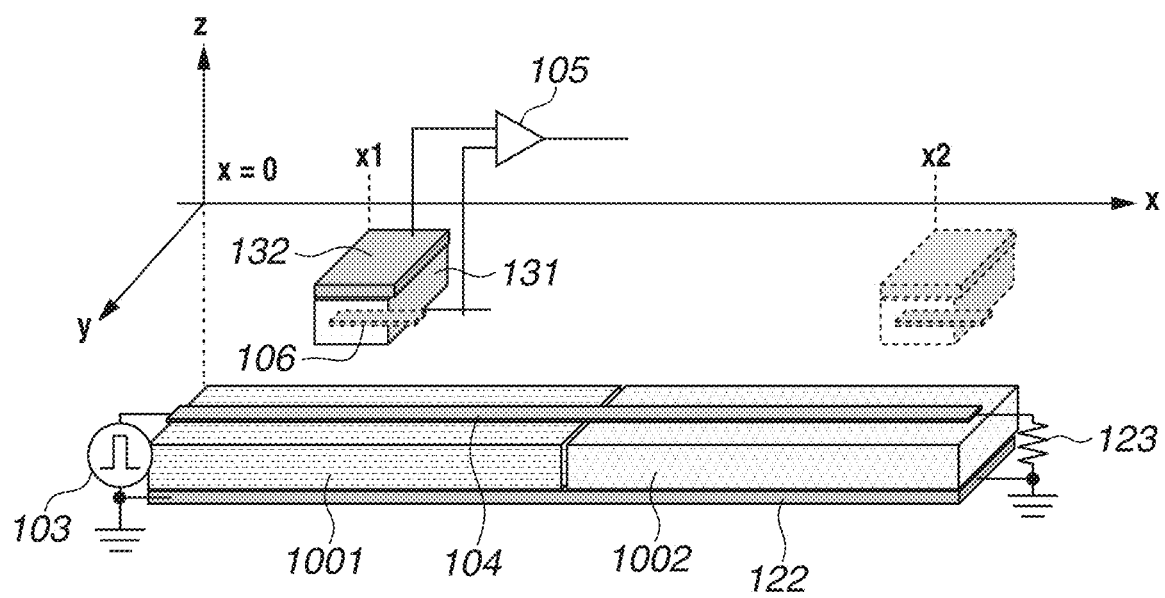
FIG. 9 is a diagram illustrating an example of a configuration of couplers and dielectric substrates.

Another example of a configuration for preventing a change in received signal intensity that is caused by a change in the positional relationship between the transmission coupler 104 and the reception coupler 106 will be described below. FIG. 9 illustrates an example of a configuration in which the dielectric substrate 121 in the configuration illustrated in FIG. 1B is replaced by dielectric substrates 1001 and 1002 arranged in the extension direction of the transmission coupler 104. More specifically, in the configuration illustrated in FIG. 9, the transmission coupler 104 is provided on the dielectric substrates 1001 and 1002. Each component similar to that in FIG. 1B is given the same reference numeral.

The dielectric substrate 1001 located closer to the input end of the transmission coupler 104 has a higher dielectric constant than that of the dielectric substrate 1002 located farther from the input end of the transmission coupler 104. Thus, in a case in which the reception coupler 106 overlaps a portion of the transmission coupler 104 that is provided on the dielectric substrate 1001 when the reception coupler 106 and the transmission coupler 104 are viewed from the z-direction (e.g., case in which the position of the reception coupler 106 in the x-direction is x1), the degree of coupling between the transmission coupler 104 and the reception coupler 106 is low. In contrast, in a case in which the reception coupler 106 overlaps a portion of the transmission coupler 104 that is provided on the dielectric substrate 1002 when the reception coupler 106 and the transmission coupler 104 are viewed from the z-direction (e.g., case in which the position of the reception coupler 106 in the x-direction is x2), the degree of coupling between the transmission coupler 104 and the reception coupler 106 is high.

Thus, with the configuration illustrated in FIG. 9, a signal received by the reception coupler 106 is prevented from being weakened by attenuation of the signal transmitted through the transmission coupler 104 in the case in which the reception coupler 106 is positioned far from the input end of the transmission coupler 104. More specifically, a change in the received signal intensity that is caused by a change in the positional relationship between the transmission coupler 104 and the reception coupler 106 is prevented. Herein, the dielectric substrate on which the transmission coupler 104 is provided includes two portions each having a different dielectric constant in the example illustrated in FIG. 9. However, the configuration is not limited to that illustrated in FIG. 9, and the dielectric substrate can include three or more portions each having a different dielectric constant. In the method illustrated in FIG. 9, use of the transmission coupler 104 having a special shape as illustrated in FIG. 3B is unnecessary. Further, the portion in which the transmission coupler 104 and the reception coupler 106 are stored in the communication system 500 is small compared to that in the method illustrated in FIGS. 3A, 5A, 5B, 6, and 8.

As described above with reference to FIGS. 1 to 9, the communication system according to the present exemplary embodiment includes the transmission coupler 104 that transmits a signal from one end portion (input end) to the other end portion in the x-direction, and the reception coupler 106 that is shorter in length in the x-direction than the transmission coupler 104. The communication system further includes the transmission circuit 103 and the reception circuit 105 that control wireless communication using the electromagnetic field coupling between the transmission coupler 104 and the reception coupler 106. The communication system further includes the movement control unit 113 that moves at least one of the transmission coupler 104 and the reception coupler 106 so as to change the position of the reception coupler 106 relative to the transmission coupler 104 in the x-direction. In the communication system, the greater the distance between the overlap portion where the transmission coupler 104 and the reception coupler 106 overlap when viewed from the z-direction vertical to the x-direction and the input end of the transmission coupler 104 is, the higher the degree of coupling between the transmission coupler 104 and the reception coupler 106 becomes.

With the above-described structure, a change in the received signal intensity that is caused by a change in the positional relationship between the transmission coupler 104 and the reception coupler 106 can be prevented. Thus, an increase in noise in a signal received in the case in which the reception coupler 106 is located in the vicinity of the input end of the transmission coupler 104 is prevented, and a signal received in the case in which the reception coupler 106 is located in the vicinity of the opposite end portion of the transmission coupler 104 with respect to the input end is prevented from becoming excessively weak. As a result, communication accuracy of the communication system in which the positional relationship between the transmission coupler 104 and the reception coupler 106 for performing wireless communication changes is improved.

The degree of coupling between the transmission coupler 104 and the reception coupler 106 does not necessarily increase linearly as the distance of the reception coupler 106 from the input end of the transmission coupler 104 increases. For example, the facing area of the transmission coupler 104 and the reception coupler 106 can be smaller in a case in which the position of the reception coupler 106 in the x-direction is within a first range in the configurations illustrated in FIGS. 3A, 3B, 5A, and 5B than in a case in which the position thereof in the x-direction is within a second range that is closer to the input end than the first range, and the facing area in each of the ranges can be fixed. Similarly, in a case in which the position of the reception coupler 106 in the x-direction is within a predetermined range in the configurations illustrated in FIGS. 6 and 8, the spacing between the transmission coupler 104 and the reception coupler 106 can be fixed.

[Adjustment by Signal Amplitude Control]

Figure 10:
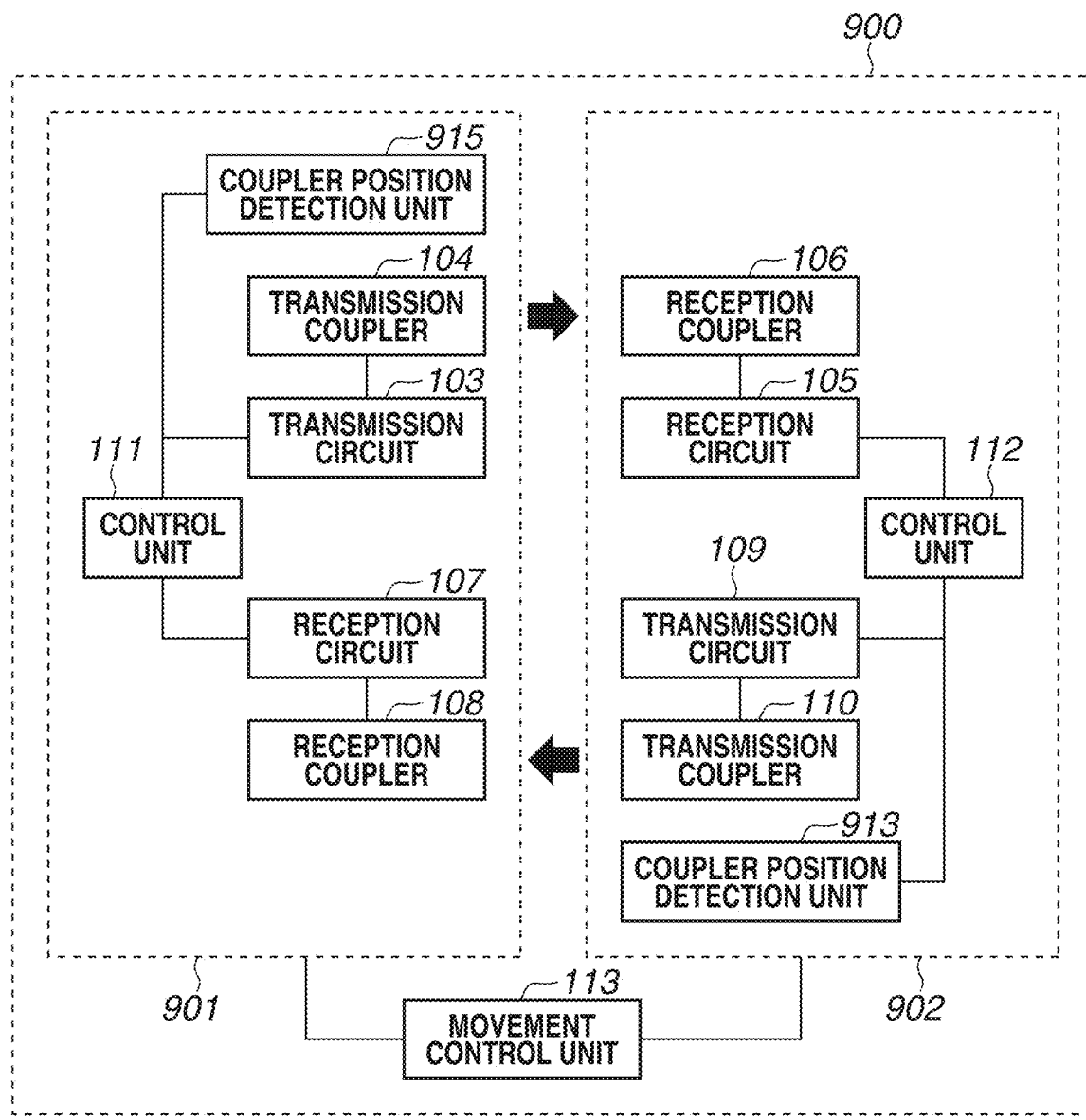
FIG. 10 is a block diagram illustrating an example of a configuration of a wireless communication system.

While the configuration for changing the degree of coupling between the transmission coupler 104 and the reception coupler 106 has been described above, there is described an example of a configuration for changing a signal amplitude to prevent a change in the received signal intensity that is caused by a change in the positional relationship between the transmission coupler 104 and the reception coupler 106. In FIG. 10, a wireless communication system 900 includes communication apparatuses 901 and 902. The communication apparatus 901 includes a coupler position detection unit 915 in addition to the configuration of the communication apparatus 101 illustrated in FIG. 1A. Similarly, the communication apparatus 902 includes a coupler position detection unit 913 in addition to the configuration of the communication apparatus 102. The configurations of the transmission coupler 104 and the reception coupler 106 are similar to those illustrated in FIG. 1B.

The coupler position detection unit 915 detects the relative position of the reception coupler 106 to the transmission coupler 104. The control unit 111 changes an amplitude of a signal input from the transmission circuit 103 to the transmission coupler 104 based on the relative position detected by the coupler position detection unit 915. For example, in a case in which the coupler position detection unit 915 detects that the position of the reception coupler 106 in the x-direction is x2 in FIG. 1B, a signal with an amplitude amplified compared to an amplitude in a case in which the coupler position detection unit 915 detects that the position is x1 is input to the input end of the transmission coupler 104.

As described above, in the wireless communication system 900, the farther the overlap portion where the transmission coupler 104 and the reception coupler 106 overlap when viewed from the z-direction is from the input end of the transmission coupler 104, the larger the amplitude of a signal input from the transmission circuit 103 to the transmission coupler 104 is set. Thus, with the configuration illustrated in FIG. 10, a signal received by the reception coupler 106 is prevented from being weakened by attenuation of the signal transmitted through the transmission coupler 104 in the case in which the reception coupler 106 is positioned far from the input end of the transmission coupler 104. In this way, a change in the received signal intensity that is caused by a change in the positional relationship between the transmission coupler 104 and the reception coupler 106 is prevented and, as a result, communication accuracy is improved.

Amplification or attenuation of the amplitude of an input signal by the transmission circuit 103 can be performed by either hardware or software. In place of or in combination with the control of the amplitude of an input signal by the transmission circuit 103, the reception circuit 105 can amplify or attenuate the amplitude of a signal output from the reception coupler 106. Further, the control unit 111 can control a threshold value of a comparator for processing a signal that is output from the reception coupler 106 in the reception circuit 105 based on the relative position detected by the coupler position detection unit 915. For example, the farther the overlap portion where the transmission coupler 104 and the reception coupler 106 overlap when viewed from the z-direction is from the input end of the transmission coupler 104, the lower the threshold value of the comparator of the reception circuit 105 is set. This method also provides a similar effect to that provided by the above-described method in which the amplitude is controlled. Further, the coupler position detection unit 915 configured to detect the relative positions of the transmission coupler 104 and the reception coupler 106 can be included not in the communication apparatus 901 but in the communication apparatus 902, and a result of detection by the coupler position detection unit 915 can be transmitted from the communication apparatus 902 to the communication apparatus 901.

In the method illustrated in FIG. 10, use of the transmission coupler 104 having a special shape as illustrated in FIG. 3B is unnecessary, and use of the plurality of different dielectric substrates as illustrated in FIG. 9 is also unnecessary. The portion in which the transmission coupler 104 and the reception coupler 106 are stored in the communication system 900 is smaller than that in the methods illustrated in FIGS. 3A, 5A, 5B, 6, and 8. On the other hand, in the above-described method for adjusting the degree of coupling between the transmission coupler 104 and the reception coupler 106, precise control of the signal amplitude or the threshold value of the comparator is unnecessary, so that the configuration of the communication system can be simplified.

Figure 11:
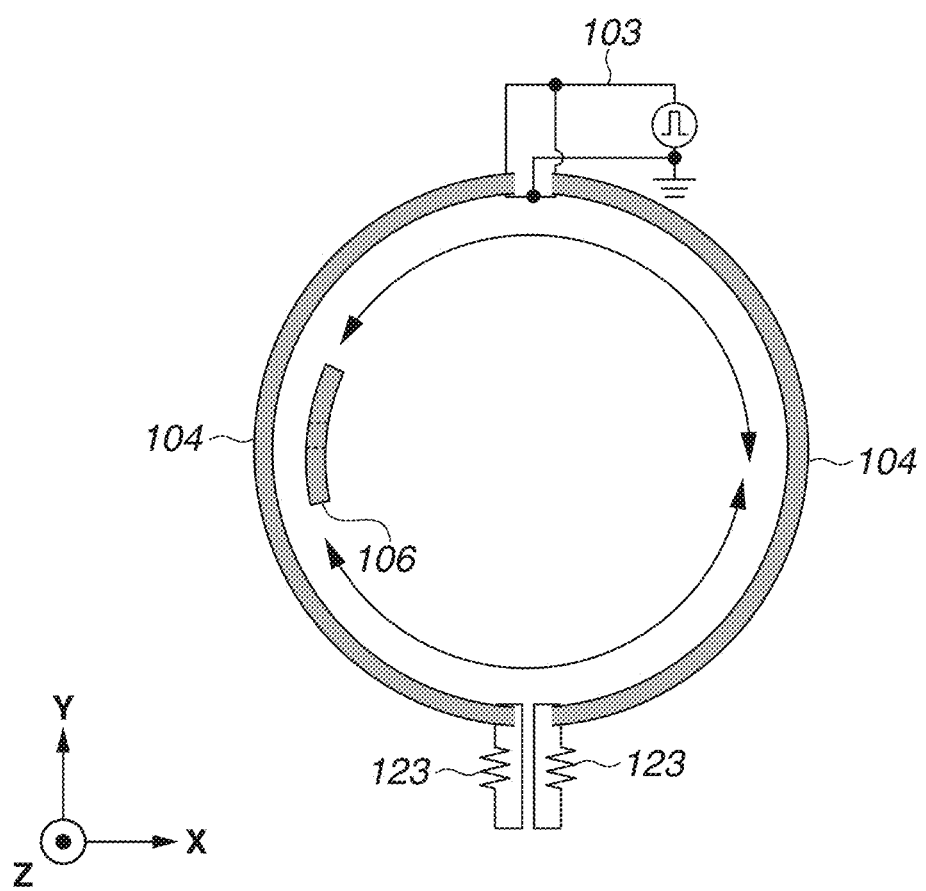
FIG. 11 is a diagram illustrating an example of a coupler configuration.

While the transmission coupler 104 is plate-shaped and a signal is transmitted on the transmission coupler 104 in a direction parallel to a surface of the transmission coupler 104 in the above description with reference to FIGS. 1 to 10, the shape of the transmission coupler 104 is not limited to that described above. For example, as illustrated in FIG. 11, the transmission coupler 104 can be ring-shaped, and a signal can be transmitted on the transmission coupler 104 in a circumferential direction of the transmission coupler 104. The movement control unit 113 can move at least one of the transmission coupler 104 and the reception coupler 106 in the circumferential direction of the transmission coupler 104. A communication system having such a configuration is applicable to, for example, a computed tomography apparatus. More specifically, the transmission coupler 104 and the reception coupler 106 are respectively mounted on fixed and rotary portions of the apparatus so that the rotary portion can communicate with the fixed portion while rotating and moving relative to the fixed portion. In this configuration, each of the above-described methods for preventing a change in the received signal intensity that is caused by a change in the positional relationship between the transmission coupler 104 and the reception coupler 106 is also applicable.

While a signal transmitted from the transmission coupler 104 is received by the reception coupler 106 that is shorter in length in the x-direction than the transmission coupler 104, in the above description, configurations of the transmission-end and the reception-end couplers can be switched. More specifically, a signal can be input to the reception coupler 106 illustrated in FIGS. 1 to 11 so that the reception coupler 106 is used as a transmission-end coupler, and the transmission coupler 104 can be used as a reception-end coupler to receive the signal. In this case, an effect similar to that of the above-described exemplary embodiment can be obtained.

The above-described methods for preventing a change in the received signal intensity that is caused by a change in the positional relationship between the transmission coupler 104 and the reception coupler 106 can be combined. For example, the spacing between the transmission coupler 104 and the reception coupler 106 can be increased and the facing area of the transmission coupler 104 and the reception coupler 106 can be reduced as the reception coupler 106 becomes closer to the input end of the transmission coupler 104. Further, in this case, the plurality of dielectric substrates each having a different dielectric constant can be used, and/or an amplitude of the input signal can be controlled. In this way, a change in the received signal intensity is further reduced.

According to the above-described exemplary embodiment, the communication accuracy is improved in a communication system in which the positional relationship between the transmission-end coupler and the reception-end coupler for performing wireless communication changes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-196232, filed Oct. 17, 2018, which is hereby incorporated by reference herein in its entirety.

What is claimed is:

1. A communication system comprising:
    a first coupler configured to transmit a signal from one end portion to another end portion in a predetermined direction;
    a second coupler that is shorter in length in the predetermined direction than the first coupler;
    a communication control unit configured to control wireless communication using electromagnetic field coupling between the first coupler and the second coupler; and
    a movement control unit configured to move at least one of the first coupler and the second coupler so as to change a position in the predetermined direction of the second coupler relative to the first coupler,
    wherein a degree of coupling between the first coupler and the second coupler is higher in a case in which a distance between a portion of the first coupler overlapping with the second coupler as viewed from a vertical direction to the predetermined direction and the one end portion of the first coupler is a first distance than the degree of coupling in a case in which the distance between a portion of the first coupler overlapping with the second coupler as viewed from the vertical direction and the one end portion of the first coupler is a second distance that is shorter than the first distance.

2. The communication system according to claim 1, wherein a spacing between the first coupler and the second coupler is smaller in the case in which the distance between the overlap portion where the first coupler and the second coupler overlap as viewed from the vertical direction and the one end portion of the first coupler is the first distance than the spacing in the case in which the distance between the overlap portion where the first coupler and the second coupler overlap as viewed from the vertical direction and the one end portion of the first coupler is the second distance.

3. The communication system according to claim 1, wherein an area of the overlap portion is larger in the case in which the distance between the overlap portion where the first coupler and the second coupler overlap as viewed from the vertical direction and the one end portion of the first coupler is the first distance than the area in the case in which the distance between the overlap portion where the first coupler and the second coupler overlap as viewed from the vertical direction and the one end portion of the first coupler is the second distance.

4. The communication system according to claim 1, wherein a width of the other end portion of the first coupler is larger than a width of the one end portion of the first coupler.

5. The communication system according to claim 1,
    wherein the first coupler is provided to a first substrate and a second substrate that are arranged in the predetermined direction,
    wherein the first substrate is farther from the one end portion of the first coupler in the predetermined direction than the second substrate, and
    wherein a dielectric constant of the first substrate is lower than a dielectric constant of the second substrate.

6. The communication system according to claim 1,
    wherein the first coupler is plate-shaped, and
    wherein the predetermined direction is a direction that is parallel to a surface of the first coupler.

7. The communication system according to claim 1,
    wherein the first coupler is ring-shaped, and
    wherein the predetermined direction is a circumferential direction of the first coupler.

8. The communication system according to claim 1, wherein the movement control unit moves at least one of the first coupler and the second coupler in the predetermined direction.

9. The communication system according to claim 1, wherein the movement control unit moves at least one of the first coupler and the second coupler so as to change a position of the second coupler relative to the first coupler in the predetermined direction and a position of the second coupler relative to the first coupler in a vertical direction to the predetermined direction.

10. The communication system according to claim 1, wherein the communication control unit controls wireless communication performed using a baseband method via the first coupler and the second coupler.

* * * * *